(12) United States Patent
Pratt et al.

(10) Patent No.: US 11,318,244 B2
(45) Date of Patent: May 3, 2022

(54) NEGATIVE PRESSURE WOUND THERAPY DEVICE WITH AUTOMATED FILTER PURGING

(71) Applicant: KCI LICENSING, INC., San Antonio, TX (US)

(72) Inventors: Benjamin A. Pratt, Poole (GB); James K. Seddon, Wimborne (GB); Christopher B. Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 194 days.

(21) Appl. No.: 16/758,275

(22) PCT Filed: Oct. 23, 2018

(86) PCT No.: PCT/US2018/057050
§ 371 (c)(1),
(2) Date: Apr. 22, 2020

(87) PCT Pub. No.: WO2019/083966
PCT Pub. Date: May 2, 2019

(65) Prior Publication Data
US 2020/0338242 A1 Oct. 29, 2020

Related U.S. Application Data

(60) Provisional application No. 62/577,579, filed on Oct. 26, 2017.

(51) Int. Cl.
*A61M 1/00* (2006.01)
(52) U.S. Cl.
CPC ............ *A61M 1/962* (2021.05); *A61M 1/742* (2021.05); *A61M 1/784* (2021.05); *A61M 2205/3344* (2013.01); *A61M 2205/3379* (2013.01)

(58) Field of Classification Search
CPC .................. A61M 1/962; A61M 1/742; A61M 2205/3344; A61M 2205/7554;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Susan S Su
*Assistant Examiner* — Eric Rassavong

(57) ABSTRACT

A negative pressure wound therapy (NPWT) device includes a canister, a pump, a filter, and a control unit. The canister is configured to collect wound exudate from a wound site. The pump is fluidly coupled to the canister and configured to draw a vacuum within the canister by pumping air out of the canister. The filter is positioned between the canister and the pump such that the air pumped out of the canister passes through the filter in a first direction. The control unit is configured to operate the pump and to purge the filter by causing airflow through the filter in a second direction, opposite the first direction.

13 Claims, 9 Drawing Sheets

(58) Field of Classification Search
CPC ............ A61M 2205/3379; A61M 1/90; A61M
1/784–79; B01D 2321/04; B01D 24/4636;
B01D 29/0079; B01D 29/0081; B01D
29/68; B01D 29/688
See application file for complete search history.

(56) References Cited

U.S. PATENT DOCUMENTS

| | | | |
|---|---|---|---|
| 2,632,443 A | | 3/1953 | Lesher |
| 2,682,873 A | | 7/1954 | Evans et al. |
| 2,910,763 A | | 11/1959 | Lauterbach |
| 2,969,057 A | | 1/1961 | Simmons |
| 3,066,672 A | | 12/1962 | Crosby, Jr. et al. |
| 3,367,332 A | | 2/1968 | Groves |
| 3,520,300 A | | 7/1970 | Flower, Jr. |
| 3,568,675 A | | 3/1971 | Harvey |
| 3,648,692 A | | 3/1972 | Wheeler |
| 3,682,180 A | | 8/1972 | McFarlane |
| 3,826,254 A | | 7/1974 | Mellor |
| 3,929,133 A | * | 12/1975 | Ragab .................... A61B 17/42 |
| | | | 604/119 |
| 4,080,970 A | | 3/1978 | Miller |
| 4,096,853 A | | 6/1978 | Weigand |
| 4,139,004 A | | 2/1979 | Gonzalez, Jr. |
| 4,165,748 A | | 8/1979 | Johnson |
| 4,184,510 A | | 1/1980 | Murry et al. |
| 4,233,969 A | | 11/1980 | Lock et al. |
| 4,245,630 A | | 1/1981 | Lloyd et al. |
| 4,256,109 A | | 3/1981 | Nichols |
| 4,261,363 A | | 4/1981 | Russo |
| 4,275,721 A | | 6/1981 | Olson |
| 4,284,079 A | | 8/1981 | Adair |
| 4,297,995 A | | 11/1981 | Golub |
| 4,333,468 A | | 6/1982 | Geist |
| 4,373,519 A | | 2/1983 | Errede et al. |
| 4,382,441 A | | 5/1983 | Svedman |
| 4,392,853 A | | 7/1983 | Muto |
| 4,392,858 A | | 7/1983 | George et al. |
| 4,419,097 A | | 12/1983 | Rowland |
| 4,465,485 A | | 8/1984 | Kashmer et al. |
| 4,475,909 A | | 10/1984 | Eisenberg |
| 4,480,638 A | | 11/1984 | Schmid |
| 4,525,166 A | | 6/1985 | Leclerc |
| 4,525,374 A | | 6/1985 | Vaillancourt |
| 4,540,412 A | | 9/1985 | Van Overloop |
| 4,543,100 A | | 9/1985 | Brodsky |
| 4,548,202 A | | 10/1985 | Duncan |
| 4,551,139 A | | 11/1985 | Plaas et al. |
| 4,569,348 A | | 2/1986 | Hasslinger |
| 4,605,399 A | | 8/1986 | Weston et al. |
| 4,608,041 A | | 8/1986 | Nielsen |
| 4,640,688 A | | 2/1987 | Hauser |
| 4,655,754 A | | 4/1987 | Richmond et al. |
| 4,664,662 A | | 5/1987 | Webster |
| 4,710,165 A | | 12/1987 | McNeil et al. |
| 4,733,659 A | | 3/1988 | Edenbaum et al. |
| 4,743,232 A | | 5/1988 | Kruger |
| 4,758,220 A | | 7/1988 | Sundblom et al. |
| 4,787,888 A | | 11/1988 | Fox |
| 4,826,494 A | | 5/1989 | Richmond et al. |
| 4,838,883 A | | 6/1989 | Matsuura |
| 4,840,187 A | | 6/1989 | Brazier |
| 4,863,449 A | | 9/1989 | Therriault et al. |
| 4,872,450 A | | 10/1989 | Austad |
| 4,878,901 A | | 11/1989 | Sachse |
| 4,897,081 A | | 1/1990 | Poirier et al. |
| 4,906,233 A | | 3/1990 | Moriuchi et al. |
| 4,906,240 A | | 3/1990 | Reed et al. |
| 4,919,654 A | | 4/1990 | Kalt |
| 4,941,882 A | | 7/1990 | Ward et al. |
| 4,953,565 A | | 9/1990 | Tachibana et al. |
| 4,969,880 A | | 11/1990 | Zamierowski |
| 4,985,019 A | | 1/1991 | Michelson |
| 5,037,397 A | | 8/1991 | Kalt et al. |
| 5,086,170 A | | 2/1992 | Luheshi et al. |
| 5,092,858 A | | 3/1992 | Benson et al. |
| 5,100,396 A | | 3/1992 | Zamierowski |
| 5,134,994 A | | 8/1992 | Say |
| 5,149,331 A | | 9/1992 | Ferdman et al. |
| 5,167,613 A | | 12/1992 | Karami et al. |
| 5,176,663 A | | 1/1993 | Svedman et al. |
| 5,215,522 A | | 6/1993 | Page et al. |
| 5,232,453 A | | 8/1993 | Plass et al. |
| 5,261,893 A | | 11/1993 | Zamierowski |
| 5,278,100 A | | 1/1994 | Doan et al. |
| 5,279,550 A | | 1/1994 | Habib et al. |
| 5,298,015 A | | 3/1994 | Komatsuzaki et al. |
| 5,342,376 A | | 8/1994 | Ruff |
| 5,344,415 A | | 9/1994 | DeBusk et al. |
| 5,358,494 A | | 10/1994 | Svedman |
| 5,437,622 A | | 8/1995 | Carion |
| 5,437,651 A | | 8/1995 | Todd et al. |
| 5,527,293 A | | 6/1996 | Zamierowski |
| 5,549,584 A | | 8/1996 | Gross |
| 5,556,375 A | | 9/1996 | Ewall |
| 5,607,388 A | | 3/1997 | Ewall |
| 5,636,643 A | | 6/1997 | Argenta et al. |
| 5,645,081 A | | 7/1997 | Argenta et al. |
| 6,071,267 A | | 6/2000 | Zamierowski |
| 6,135,116 A | | 10/2000 | Vogel et al. |
| 6,241,747 B1 | | 6/2001 | Ruff |
| 6,287,316 B1 | | 9/2001 | Agarwal et al. |
| 6,345,623 B1 | | 2/2002 | Heaton et al. |
| 6,488,643 B1 | | 12/2002 | Tumey et al. |
| 6,493,568 B1 | | 12/2002 | Bell et al. |
| 6,553,998 B2 | | 4/2003 | Heaton et al. |
| 6,814,079 B2 | | 11/2004 | Heaton et al. |
| 7,004,915 B2 | * | 2/2006 | Boynton ................ A61M 1/73 |
| | | | 601/6 |
| 7,651,484 B2 | | 1/2010 | Heaton et al. |
| 8,394,081 B2 | | 3/2013 | Locke et al. |
| 9,446,178 B2 | * | 9/2016 | Blott ...................... A61M 1/85 |
| 2002/0077661 A1 | | 6/2002 | Saadat |
| 2002/0115951 A1 | | 8/2002 | Norstrem et al. |
| 2002/0120185 A1 | | 8/2002 | Johnson |
| 2002/0143286 A1 | | 10/2002 | Tumey |
| 2014/0163487 A1 | | 6/2014 | Tout et al. |
| 2014/0163489 A1 | * | 6/2014 | Walti .................... A61M 1/0058 |
| | | | 604/319 |
| 2015/0025485 A1 | * | 1/2015 | Luckemeyer ......... G01F 23/2966 |
| | | | 604/319 |
| 2016/0015871 A1 | * | 1/2016 | Locke ..................... A61M 1/85 |
| | | | 604/290 |
| 2016/0045648 A1 | * | 2/2016 | Locke ..................... A61M 1/90 |
| | | | 604/318 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |

(56) References Cited

FOREIGN PATENT DOCUMENTS

| WO | 97/18007 A1 | 5/1997 | |
|---|---|---|---|
| WO | 99/13793 A1 | 3/1999 | |
| WO | WO-2008/012278 A1 | 1/2008 | |
| WO | WO-2009/046403 A1 | 4/2009 | |
| WO | WO-2017180467 A1 * | 10/2017 | .............. A61M 1/85 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., JR., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax, "Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in Il All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
International Search Report and Written Opinion in International Application No. PCT/US2018/057050, dated Jan. 7, 2019. (16 pages).

* cited by examiner

NEGATIVE PRESSURE WOUND THERAPY DEVICE WITH AUTOMATED FILTER PURGING

CROSS-REFERENCE TO RELATED APPLICATIONS

This application claims the benefit of priority to international patent application number PCT/US2018/057050, having a filing date of Oct. 23, 2018, which claims the benefit of priority to U.S. Provisional Application No. 62/577,579, filed on Oct. 26, 2017, which are both incorporated herein by reference in theirs entirety.

BACKGROUND

The present disclosure relates generally to wound therapy systems and devices, and more particularly to a negative pressure wound therapy device.

Negative pressure wound therapy (NPWT) is a type of wound therapy that involves applying negative pressure (relative to atmospheric pressure) to a wound site to promote wound healing. Some NPWT systems include a pump which operates to maintain the wound site at negative pressure by removing wound exudate from the wound site. The wound exudate is typically routed to a canister or other container fluidly connected to the pump where the wound exudate is stored until emptied by a user.

Hydrophobic filters are an integral part of canister design and functionality. However, such filters can degrade or become blocked over time. For example, a broken filter can cause damage to the pump. Coating of the filter with fluids, fats, and protein can cause the filter to lose open flow area over time and can limit the life of the canister.

SUMMARY

One implementation of the present disclosure is a negative pressure wound therapy (NPWT) device including a canister, a pump, a filter, and a control unit. The canister is configured to collect wound exudate from a wound site. The pump is fluidly coupled to the canister and configured to draw a vacuum within the canister by pumping air out of the canister. The filter is positioned between the canister and the pump such that the air pumped out of the canister passes through the filter in a first direction. The control unit is configured to operate the pump and to purge the filter by causing airflow through the filter in a second direction, opposite the first direction.

In some embodiments, the NPWT device includes a purge valve fluidly connected with the pump and the filter. The control unit can be configured to operate the purge valve to cause the airflow through the filter in the second direction. In some embodiments, the control unit is configured to purge the filter by operating the pump to draw a vacuum within the canister and opening the purge valve to allow airflow into the canister. The airflow may fill the vacuum within the canister and pass through the filter in the second direction.

In some embodiments, the control unit is configured to determine an amount of dead-space within the canister by operating the pump to reduce a pressure within the canister to a first pressure threshold and opening the purge valve to allow airflow into the canister. The airflow may cause the pressure within the canister to increase. The control unit can monitor an amount of time required for the pressure within the canister to increase from the first pressure threshold to a second pressure threshold and can determine the amount of dead-space within the canister based on the amount of time. In some embodiments, wherein the dead-space within the canister includes an internal volume of the canister not occupied by the wound exudate.

In some embodiments, the control unit is configured to operate the pump in a forward operating mode to cause the airflow through the filter in the first direction and operate the pump in a reverse operating mode to cause the airflow through the filter in the second direction.

In some embodiments, the NPWT device includes a pressure sensor configured to measure a pressure within the canister or at the wound site. In some embodiments, the control unit is configured to activate the pump to reduce the measured pressure to a target pressure, deactivate the pump upon detecting that the measured pressure has reached the target pressure, determine whether the target pressure is maintained for a predetermined amount of time after deactivating the pump, and in response to a determination that the target pressure is maintained for the predetermined amount of time, purge the filter by causing the airflow through the filter in a second direction.

In some embodiments, the control unit is configured to determine that a wound exudate draining process has completed in response to the determination that the target pressure is maintained for the predetermined amount of time and purge the filter in response to a determination that the draining process has completed.

In some embodiments, the control unit is configured to perform a dead-space detection operation to determine an amount of dead-space within the canister in response to the determination that the target pressure is maintained for the predetermined amount of time and purge the filter after performing the dead-space detection operation.

In some embodiments, the NPWT device includes a canister sensor configured to detect whether the canister is present. The control unit can be configured to determine whether the canister is present based on input from the canister sensor and can activate the pump in response to a determination that the canister is present.

In some embodiments, the NPWT device includes an orientation sensor configured to detect an orientation of at least one of the canister or the negative pressure wound therapy device. The control unit can be configured to determine the orientation based on input from the orientation sensor and activate the pump in response to a determination that the orientation is acceptable. In some embodiments, the orientation sensor is an accelerometer configured to measure the orientation relative to a direction of gravity.

In some embodiments, the control unit is configured to start a timer in response to a determination that the orientation is not acceptable and, upon expiration of the timer, use new input from the orientation sensor to determine whether the orientation is acceptable.

In some embodiments, the control unit is configured to increment a counter in response to a determination that the orientation is not acceptable, compare the counter to a threshold value, and generate an orientation alert in response to a determination that the counter has reached the threshold value.

Another implementation of the present disclosure is a method for operating a negative pressure wound therapy (NPWT) device. The method includes collecting wound exudate from a wound site in a canister and operating a pump to draw a vacuum within the canister by pumping air out of the canister. The air pumped out of the canister passes through a filter in a first direction. The method further includes purging the filter by causing airflow through the filter in a second direction, opposite the first direction.

In some embodiments, purging the filter includes operating a purge valve fluidly connected with the pump and the filter to cause the airflow through the filter in the second direction. In some embodiments, purging the filter includes opening a purge valve to allow airflow into the canister, the airflow filling the vacuum within the canister and passing through the filter in the second direction.

In some embodiments, the method includes operating the pump to reduce a pressure within the canister to a first pressure threshold and opening a valve to allow airflow into the canister. The airflow may cause the pressure within the canister to increase. The method may include monitoring an amount of time required for the pressure within the canister to increase from the first pressure threshold to a second pressure threshold and determining an amount of dead-space within the canister based on the amount of time. In some embodiments, the dead-space within the canister comprises an internal volume of the canister not occupied by the wound exudate.

In some embodiments, the method includes operating the pump in a forward operating mode to cause the airflow through the filter in the first direction and operating the pump in a reverse operating mode to cause the airflow through the filter in the second direction.

In some embodiments, using a pressure sensor to measure a pressure within the canister or at the wound site. The method may include activating the pump to reduce the measured pressure to a target pressure, deactivating the pump upon detecting that the measured pressure has reached the target pressure, determining whether the target pressure is maintained for a predetermined amount of time after deactivating the pump, and in response to a determination that the target pressure is maintained for the predetermined amount of time, purging the filter by causing the airflow through the filter in a second direction.

In some embodiments, the method includes determining that a wound exudate draining process has completed in response to the determination that the target pressure is maintained for the predetermined amount of time and purging the filter in response to a determination that the draining process has completed.

In some embodiments, the method includes performing a dead-space detection operation to determine an amount of dead-space within the canister in response to the determination that the target pressure is maintained for the predetermined amount of time and purging the filter after performing the dead-space detection operation.

In some embodiments, the method includes determining whether the canister is present based on input from a canister sensor and activating the pump in response to a determination that the canister is present.

In some embodiments, determining an orientation of at least one of the canister or the negative pressure wound therapy device using input from an orientation sensor and activating the pump in response to a determination that the orientation is acceptable. In some embodiments, the orientation sensor is an accelerometer configured to measure the orientation relative to a direction of gravity.

In some embodiments, the method includes starting a timer in response to a determination that the orientation is not acceptable and, upon expiration of the timer, using new input from the orientation sensor to determine whether the orientation is acceptable.

In some embodiments, the method includes incrementing a counter in response to a determination that the orientation is not acceptable, comparing the counter to a threshold value, and generating an orientation alert in response to a determination that the counter has reached the threshold value.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Overview

Referring generally to the FIGURES, a negative pressure wound therapy (NPWT) device and components thereof are shown, according to various exemplary embodiments. The NPWT device may include a canister, a pump, a filter, and a control unit. The canister can be configured to collect wound exudate from a wound site. The pump can be fluidly coupled to the canister and configured to draw a vacuum within the canister by pumping air out of the canister. The filter may be positioned between the canister and the pump such that the air pumped out of the canister passes through the filter in a first direction. The control unit can be configured to operate the pump and to purge the filter by causing airflow through the filter in a second direction, opposite the first direction. In some embodiments, the NPWT device includes a valve configured to control airflow into the NPWT device from the ambient environment. The valve can be opened by the control unit to cause the airflow through the filter in the second direction.

In some embodiments, purging the filter includes removing liquids, fats, proteins, or other substances which may accumulate in the filter over time. The purging process may increase the open flow area through the filter and can substantially extend the life of the filter and/or the canister. Advantageously, the purging process may use reverse airflow through the filter, which may be less damaging to the filter than mechanical purging.

In some embodiments, the purging process performed by the control unit involves operating both the pump and the valve. For example, the control unit can close the valve and operate the pump to draw a vacuum within the canister. Drawing a vacuum within the canister may include pumping air out of the canister, through the filter. After a vacuum has been drawn within the canister, the control unit can open the valve to allow airflow into the NPWT device from the environment around the NPWT device. The airflow may pass through the filter in a reverse direction to fill the vacuum within the canister, thereby purging the filter.

In other embodiments, the control unit can purge the filter without operating the valve. For example, the control unit can operate the pump in a forward direction to draw a vacuum within the canister. To purge the filter, the control unit can operate the pump in a reverse direction to cause reverse airflow through the filter in a reverse direction. In this embodiment, the valve may remain closed throughout the purging process or can be omitted from the NPWT device entirely. These and other features and advantages of the NPWT device are described in detail below.

Negative Pressure Wound Therapy System

Figure 1:
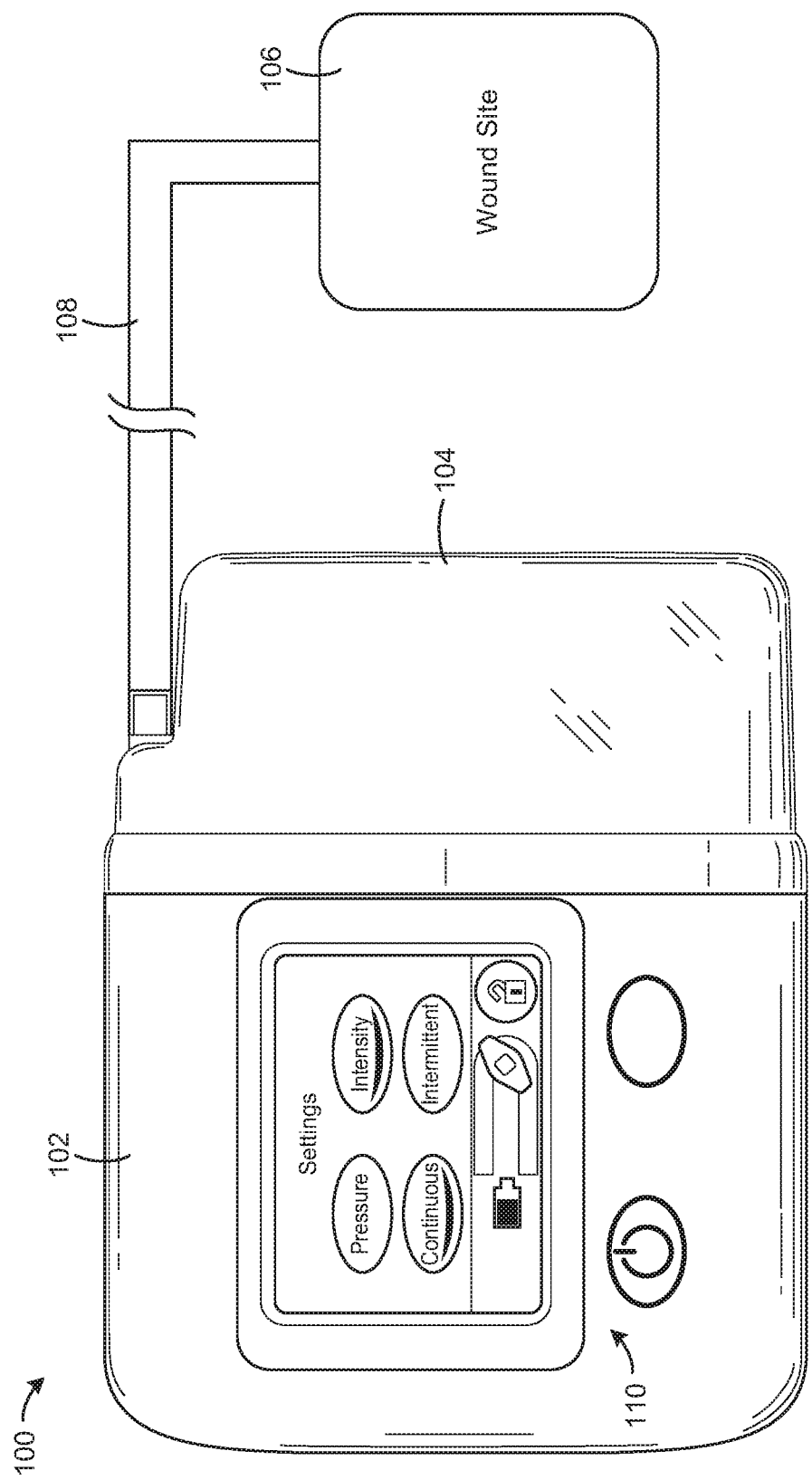
FIG. 1 is a drawing of a negative pressure wound therapy (NPWT) system including a NPWT device fluidly connected with a wound site, according to an exemplary embodiment.
Figure 2:
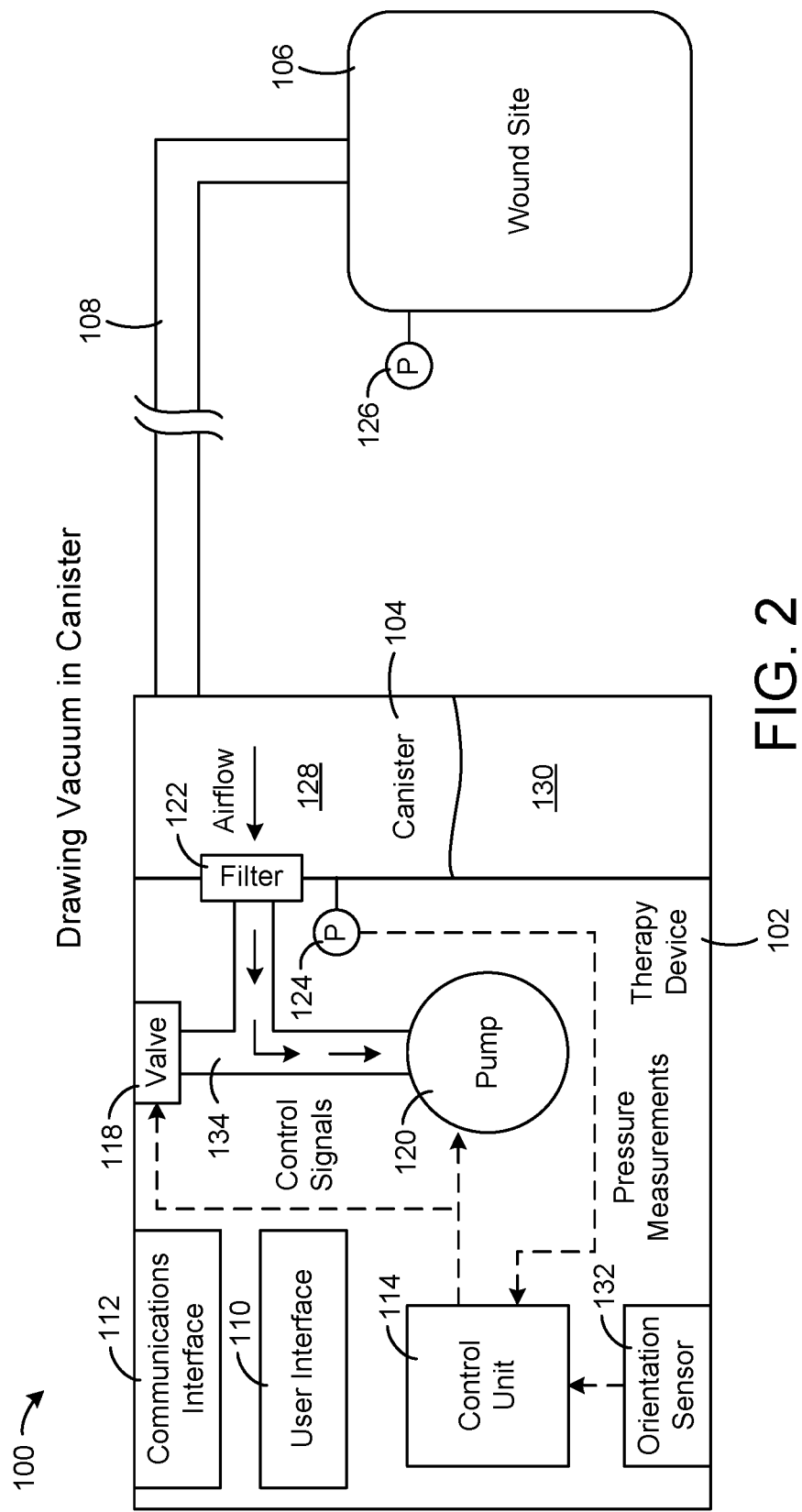
FIG. 2 is a block diagram illustrating the operation of NPWT device of FIG. 1 in greater detail when drawing a vacuum within a canister of the NPWT device, according to an exemplary embodiment.
Figure 3:
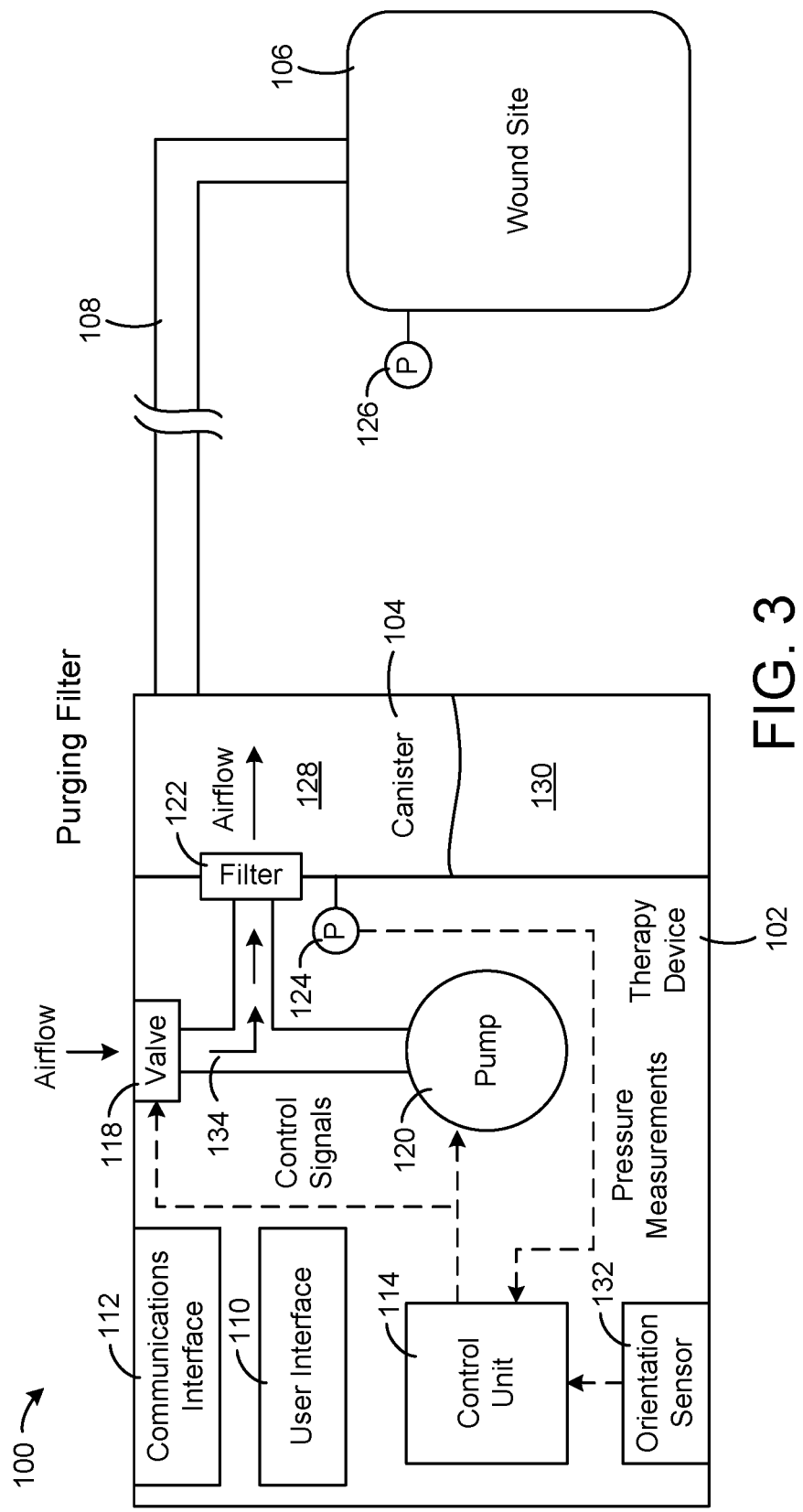
FIG. 3 is a block diagram illustrating the operation of NPWT device of FIG. 1 in greater detail when purging a filter of the NPWT device, according to an exemplary embodiment.

Referring now to FIGS. 1-3, a negative pressure wound therapy (NPWT) system 100 is shown, according to an exemplary embodiment. NPWT system 100 is shown to include a therapy device 102 fluidly connected to a wound site 106 via tubing 108. Wound site 106 may include a tissue wound as well as a wound dressing that covers the tissue wound and adheres to a patient's skin. Several examples of wound dressings which can be used in combination with NPWT system 100 are described in detail in U.S. Pat. No. 7,651,484 granted Jan. 26, 2010, U.S. Pat. No. 8,394,081 granted Mar. 12, 2013, and U.S. patent application Ser. No. 14/087,418 filed Nov. 22, 2013. The entire disclosure of each of these patents and patent applications is incorporated by reference herein.

Therapy device 102 can be configured to provide negative pressure wound therapy by reducing the pressure at wound site 106. Therapy device 102 can draw a vacuum at wound site 106 (relative to atmospheric pressure) by removing wound exudate, air, and other fluids from wound site 106. Wound exudate may include fluid that filters from a patient's circulatory system into lesions or areas of inflammation. For example, wound exudate may include water and dissolved solutes such as blood, plasma proteins, white blood cells, platelets, and red blood cells. Other fluids removed from wound site 106 may include instillation fluid previously delivered to wound site 106. Instillation fluid can include, for example, a cleansing fluid, a prescribed fluid, a medicated fluid, an antibiotic fluid, or any other type of fluid which can be delivered to wound site 106 during wound treatment.

The fluids removed from wound site 106 pass through tubing 108 and are collected in canister 104. Canister 104 may be a component of therapy device 102 configured to collect wound exudate and other fluids removed from wound site 106. In some embodiments, canister 104 is detachable from therapy device 102 to allow canister 104 to be emptied and replaced as needed. A lower portion 130 of canister 104 may be filled with wound exudate and other fluids removed from wound site 106, whereas an upper portion 128 of canister 104 may be filled with air. Therapy device 102 can be configured to draw a vacuum within canister 104 by pumping air out of canister 104. The reduced pressure within canister 104 can be translated to wound site 106 via tubing 108 such that wound site 106 is maintained at the same pressure as canister 104.

Referring particularly to FIGS. 2-3, block diagrams illustrating therapy device 102 in greater detail are shown, according to an exemplary embodiment. Therapy device 102 is shown to include a pump 120, a filter 122, a valve 118, and a control unit 114. Pump 120 can be fluidly coupled to canister 104 (e.g., via conduit 134) and can be configured to draw a vacuum within canister 104 by pumping air out of canister 104. In some embodiments, pump 120 is configured to operate in both a forward direction and a reverse direction. For example, pump 120 can operate in the forward direction to pump air out of canister 104 and decrease the pressure within canister 104. Pump 120 can operate in the reverse direction to pump air into canister 104 and increase the pressure within canister 104. Pump 120 can be controlled by control unit 114, described in greater detail below.

In some embodiments, pump 120 is a peristaltic pump having a rotor and one or more head rollers. The rotor can be configured to rotate in a forward direction to pump air out of canister 104 and/or in a reverse direction to pump air into canister 104. Conduit 134 may pass through pump 120 and may be wrapped around the rotor and head rollers. The head rollers can be configured to seal conduit 134 against an internal surface of pump 120 (e.g., by pinching conduit 134 between the internal surface and the head rollers). When the rotor rotates, the head rollers may move along the external surface of conduit 134, thereby causing airflow through conduit 134 via peristaltic action. In other embodiments, pump 120 is a non-peristaltic pump or any other type of pump configured to pump air out of canister 104 and/or into canister 104.

Filter 122 can be positioned between canister 104 and pump 120 (e.g., along conduit 134) such that the air pumped out of canister 104 passes through filter 122. Filter 122 can be configured to prevent liquid or solid particles from entering conduit 134 and reaching pump 120. Filter 122 may include, for example, a bacterial filter that is hydrophobic and/or lipophilic such that aqueous and/or oily liquids will bead on the surface of filter 122. Pump 120 can be configured to provide sufficient airflow through filter 122 that the pressure drop across filter 122 is not substantial (e.g., such that the pressure drop will not substantially interfere with the application of negative pressure to wound site 106 from therapy device 102).

Valve 118 can be fluidly connected with pump 120 and filter 122 via conduit 134. In some embodiments, valve 118 is configured to control airflow between conduit 134 and the environment around therapy device 102. For example, valve 118 can be opened to allow airflow between conduit 134 and the environment around therapy device 102, and closed to prevent airflow between conduit 134 and the environment around therapy device 102. Valve 118 can be opened and closed by control unit 114, described in greater detail below. When valve 118 is closed, pump 120 can draw a vacuum within conduit 134 and canister 104 by causing airflow through filter 122 in a first direction, as shown in FIG. 2. When valve 118 is open, airflow from the environment around therapy device 102 may enter conduit 134 and fill the vacuum within conduit 134 and canister 104. The airflow from conduit 134 into canister 104 may pass through filter 122 in a second direction, opposite the first direction, as shown in FIG. 3.

Control unit 114 can be configured to operate pump 120, valve 118, and/or other controllable components of therapy device 102. In some embodiments, control unit 114 is configured to operate pump 120 and valve 118 to perform a purging process. The purging process can be performed to purge filter 122 of liquids, fats, proteins, or other substances which may accumulate in filter 122 over time. The purging process may increase the open flow area through filter 122 and can substantially extend the life of filter 122 and/or canister 104. Advantageously, the purging process may use reverse airflow through filter 122, which may be less damaging to filter 122 than mechanical purging.

In some embodiments, the purging process performed by control unit 114 involves operating both pump 120 and valve 118. Control unit 114 can close valve 118 and operate pump 120 to draw a vacuum within conduit 134 and canister 104. Drawing a vacuum within canister 104 may include pumping air out of canister 104, through filter 122. FIG. 2 shows the direction of the airflow through filter 122 when drawing a vacuum within canister 104 (i.e., from canister 104 into conduit 134). After a vacuum has been drawn within canister 104, control unit 114 can open valve 118 to allow airflow into conduit 134 from the environment around therapy device 102. The airflow may fill the vacuum within conduit 134 and may pass through filter 122 to fill the vacuum within canister 104. FIG. 3 shows the direction of the airflow through filter 122 when purging filter 122 (i.e., from conduit 134 into canister 104).

In other embodiments, control unit 114 can purge filter 122 without operating valve 118. For example, control unit 114 can operate pump 120 in a forward direction to draw a vacuum within conduit 134 and canister 104 (as shown in FIG. 2). To purge filter 122, control unit 114 can operate pump 120 in a reverse direction to cause reverse airflow through filter 122 (as shown in FIG. 3). In this embodiment, valve 118 may remain closed throughout the purging process or can be omitted from therapy device 102 entirely.

In some embodiments, therapy device 102 includes a variety of sensors. For example, therapy device 102 is shown to include a pressure sensor 124 configured to measure the pressure within canister 104 and an orientation sensor 132 configured to measure the orientation of therapy device 102. Orientation sensor 132 may include an accelerometer or other type of sensor configured to measure the orientation relative to a direction of gravity. In some embodiments, therapy device 102 includes a canister sensor configured to detect whether canister 104 is present (e.g., properly coupled to therapy device 102) or not present (e.g., removed for emptying). In some embodiments, system 100 includes a pressure sensor 126 configured to measure the pressure at wound site 106. Pressure measurements recorded by pressure sensors 124-126, orientation measurements recorded by orientation sensor 132, and canister measurements recorded by the canister sensor can be communicated to control unit 114. Control unit 114 can use the measurements as inputs to various control operations performed by control unit 114 (described in greater detail with reference to FIGS. 4-10).

In some embodiments, therapy device 102 includes a user interface 110. User interface 110 may include one or more buttons, dials, sliders, keys, or other input devices configured to receive input from a user. User interface 110 may also include one or more display devices (e.g., LEDs, LCD displays, etc.), speakers, tactile feedback devices, or other output devices configured to provide information to a user. In some embodiments, the pressure measurements recorded by pressure sensors 124-126 and the orientation measurements recorded by orientation sensor 132 are presented to a user via user interface 110. User interface 110 can also display alerts generated by control unit 114. For example, control unit 114 can generate an orientation alert if an improper orientation is detected by orientation sensor 132 and/or a "no canister" alert if canister 104 is not detected.

In some embodiments, therapy device 102 includes a data communications interface 112 (e.g., a USB port, a wireless transceiver, etc.) configured to receive and transmit data. Communications interface 112 may include wired or wireless communications interfaces (e.g., jacks, antennas, transmitters, receivers, transceivers, wire terminals, etc.) for conducting data communications external systems or devices. In various embodiments, the communications may be direct (e.g., local wired or wireless communications) or via a communications network (e.g., a WAN, the Internet, a cellular network, etc.). For example, communications interface 112 can include a USB port or an Ethernet card and port for sending and receiving data via an Ethernet-based communications link or network. In another example, communications interface 112 can include a Wi-Fi transceiver for communicating via a wireless communications network or cellular or mobile phone communications transceivers.

Control Unit

Figure 4:
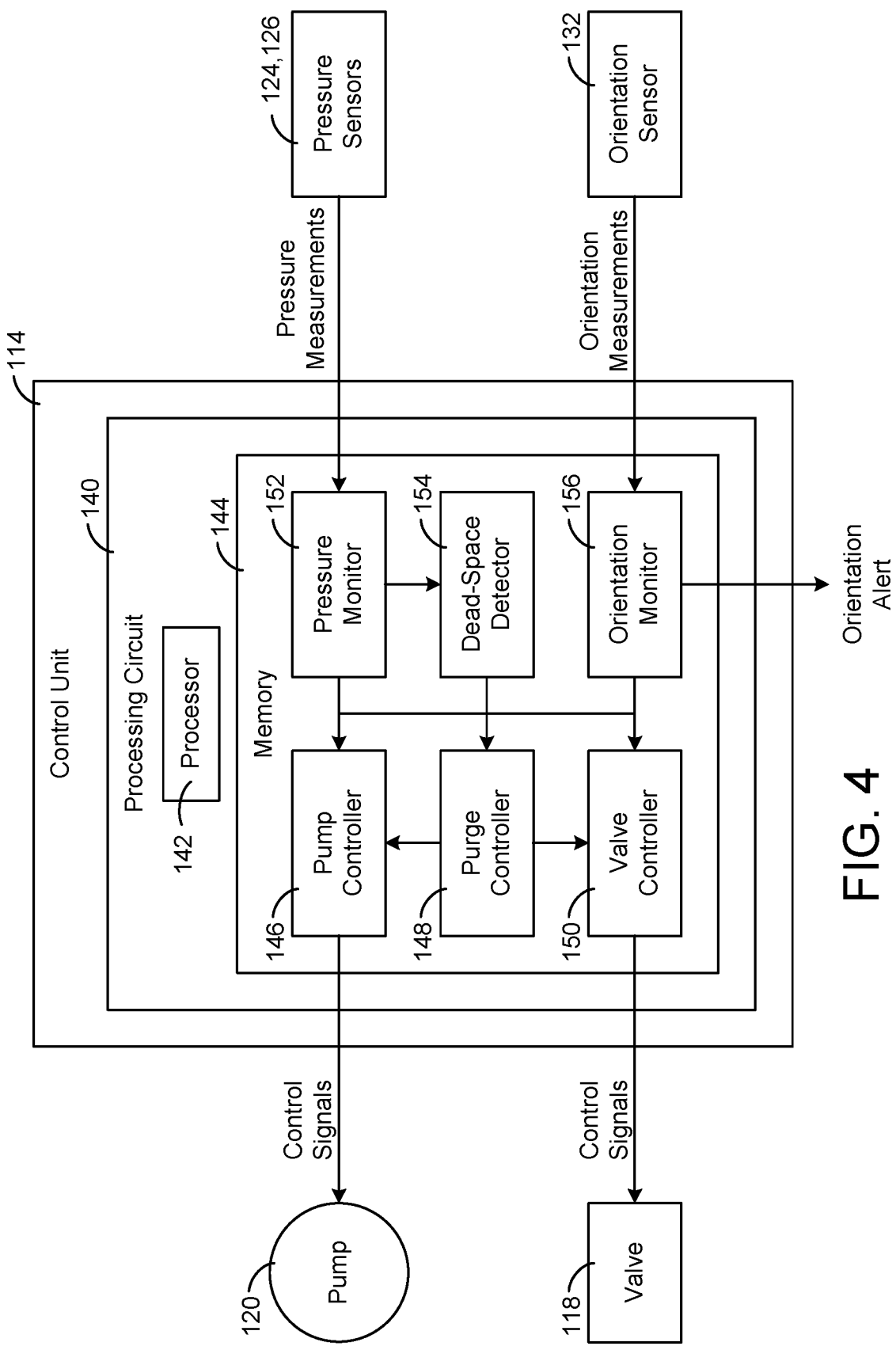
FIG. 4 is a block diagram illustrating a control unit of the NPWT device of FIG. 1 in greater detail, according to an exemplary embodiment.

Referring now to FIG. 4, a block diagram illustrating control unit 114 in greater detail is shown, according to an exemplary embodiment. Control unit 114 is shown to include a processing circuit 140 including a processor 142 and memory 144. Processor 142 may be a general purpose or specific purpose processor, an application specific integrated circuit (ASIC), one or more field programmable gate arrays (FPGAs), a group of processing components, or other suitable processing components. Processor 142 is configured to execute computer code or instructions stored in memory 144 or received from other computer readable media (e.g., CDROM, network storage, a remote server, etc.).

Memory 144 may include one or more devices (e.g., memory units, memory devices, storage devices, etc.) for storing data and/or computer code for completing and/or facilitating the various processes described in the present disclosure. Memory 144 may include random access memory (RAM), read-only memory (ROM), hard drive storage, temporary storage, non-volatile memory, flash memory, optical memory, or any other suitable memory for storing software objects and/or computer instructions. Memory 144 may include database components, object code components, script components, or any other type of information structure for supporting the various activities and information structures described in the present disclosure. Memory 144 may be communicably connected to processor 142 via processing circuit 140 and may include computer code for executing (e.g., by processor 142) one or more processes described herein. When processor 142 executes instructions stored in memory 144, processor 142 generally configures control unit 114 (and more particularly processing circuit 140) to complete such activities.

Control unit 114 is shown to include a pump controller 146 and a valve controller 150. Pump controller 146 can be configured to operate pump 120 by generating and providing control signals to pump 120. The control signals provided to pump 120 can cause pump 120 to activate, deactivate, or achieve a variable capacity or speed (e.g., operate at half speed, operate at full speed, etc.). Similarly, valve controller 150 can be configured to operate valve 118 by generating and providing control signals to valve 118. The control signals provided to valve 118 can cause valve 118 to open, close, or achieve a specified intermediate position (e.g., one-third open, half open, etc.). In some embodiments, pump controller 146 and valve controller 150 are used by other components of control unit 114 (e.g., purge controller 148, dead-space detector 154, etc.) to operate pump 120 and valve 118 when carrying out the processes described herein.

In some embodiments, pump controller 146 uses input from a canister sensor configured to detect whether canister 104 is present. Pump controller 146 can be configured to activate pump 120 only when canister 104 is present. For example, pump controller 146 can check whether canister 104 is present and can activate pump 120 in response to a determination that canister 104 is present. However, if canister 104 is not present, pump controller 146 may prevent pump 120 from activating.

Control unit 114 is shown to include a pressure monitor 152 and an orientation monitor 156. Pressure monitor 152 can be configured to monitor the pressure within canister 104 and/or the pressure at wound site 106 using feedback from pressure sensors 124-126. For example, pressure sensors 124-126 may provide pressure measurements to pressure monitor 152. Pressure monitor 152 can use the pressure measurements to determine the pressure within canister 104 and/or the pressure at wound site 106 in real-time. Pressure monitor 152 can provide the pressure value to dead-space detector 154, pump controller 146, purge controller 148, and/or valve controller 150 for use as an input to control processes performed by such components.

Orientation monitor 156 can be configured to monitor the orientation of canister 104 and/or the orientation of therapy device 102 using feedback from orientation sensor 132. For example, orientation sensor 132 may provide orientation measurements to orientation monitor 156. Orientation monitor 156 can use the orientation measurements to determine the orientation of canister 104 and/or the orientation of therapy device 102 in real-time. Orientation monitor 156 can provide the orientation value to dead-space detector 154, pump controller 146, purge controller 148, and/or valve controller 150 for use as an input to control processes performed by such components. In some embodiments, orientation monitor 156 generates an orientation alert in response to a determination that the detected orientation is not acceptable (e.g., rotated by more than a predetermined number of degrees relative to upright). In some embodiments, orientation monitor In some embodiments, pump controller 146 is configured to activate pump 120 only when the detected orientation is acceptable. For example, pump controller 146 can receive input from orientation monitor 156 indicating whether the orientation of canister 104 and/or the orientation of therapy device 102 is within acceptable bounds and can activate pump 120 in response to a determination that the orientation is acceptable. However, if the detected orientation is not acceptable, pump controller 146 may prevent pump 120 from activating.

In some embodiments, orientation monitor 156 is configured to start a timer in response to a determination that the orientation is not acceptable. Upon expiration of the timer, orientation monitor 156 can use new input from orientation sensor 132 to determine whether the orientation has changed to become acceptable. In some embodiments, orientation monitor 156 is configured to increment a counter in response to a determination that the orientation is not acceptable. Orientation monitor 156 can compare the counter to a threshold value and generate an orientation alert in response to a determination that the counter has reached the threshold value.

Purge controller 148 can be configured to purge filter 122 by causing reverse airflow through filter 122. In some embodiments, purge controller 148 operates both valve 118 and pump 120 to purge filter 122. For example, purge controller 148 can close valve 118 and operate pump 120 to draw a vacuum within conduit 134 and canister 104. After a vacuum has been drawn within canister 104, purge controller 148 can open valve 118 to allow airflow into conduit 134 from the environment around therapy device 102. The airflow may fill the vacuum within conduit 134 and may pass through filter 122 in a reverse direction to fill the vacuum within canister 104, thereby purging filter 122. In other embodiments, purge controller 148 can purge filter 122 without operating valve 118. For example, purge controller 148 can operate pump 120 in a reverse direction to cause reverse airflow through filter 122, thereby purging filter 122.

In some embodiments, purge controller 148 is configured to purge filter 122 in response to various triggers. One such trigger is a determination that the pressure within canister 104 is stable. For example, purge controller 148 can activate pump 120 to reduce the measured pressure to a target pressure and can deactivate pump 120 upon detecting that the measured pressure has reached the target pressure. Purge controller 148 can determine whether the target pressure is maintained for a predetermined amount of time after deactivating pump 120. In response to a determination that the target pressure is maintained for the predetermined amount of time, purge controller 148 can purge filter 122 by causing reverse airflow through filter 122.

In some embodiments, purge controller 148 is configured to determine that a wound exudate draining process has completed in response to the determination that the target pressure is maintained for the predetermined amount of time. Purge controller 148 can be configured to purge filter 122 in response to a determination that the draining process has completed. In some embodiments, purge controller 148 triggers dead-space detector 154 to perform a dead-space detection operation (described in greater detail below) in response to the determination that the target pressure is maintained for the predetermined amount of time. Purge controller 148 can be configured to purge filter 122 after performing the dead-space detection operation.

Dead-space detector 154 can be configured to determine an amount of dead-space within canister 104. The dead-space within canister 104 may include the internal volume of canister 104 not occupied by wound exudate. For example, the dead-space within canister 104 may include the volume of canister 104 occupied by air. In some embodiments, dead-space detector 154 is configured to determine the amount of dead-space by operating pump 120 to reduce the pressure within canister 104 to a first pressure threshold. Dead-space detector 154 can then open valve 118 to allow airflow into canister 104. The airflow may cause the pressure within canister 104 to increase. Dead-space detector 154 can monitor an amount of time required for the pressure within canister 104 to increase from the first pressure threshold to a second pressure threshold. The amount of time required for the pressure to change from the first threshold to the second threshold may be proportional (or otherwise related) to the amount of dead-space within canister 104. Accordingly, dead-space detector 154 can determine the amount of dead-space within canister 104 based on the amount of time.

In some embodiments, dead-space detector 154 determines whether the amount of dead-space within canister 104 is sufficient to hold the amount of fluid withdrawn from wound site 106. For example, dead-space detector 154 can monitor the amount of dead-space in canister 104 over time and can estimate when canister 104 will be full based on the rate at which the amount of dead-space is decreasing. Dead-space detector 154 can be configured to generate an alert or notification indicating when canister 104 will be full and can suggest that canister 104 be emptied or replaced.

Control Processes

Figure 5:
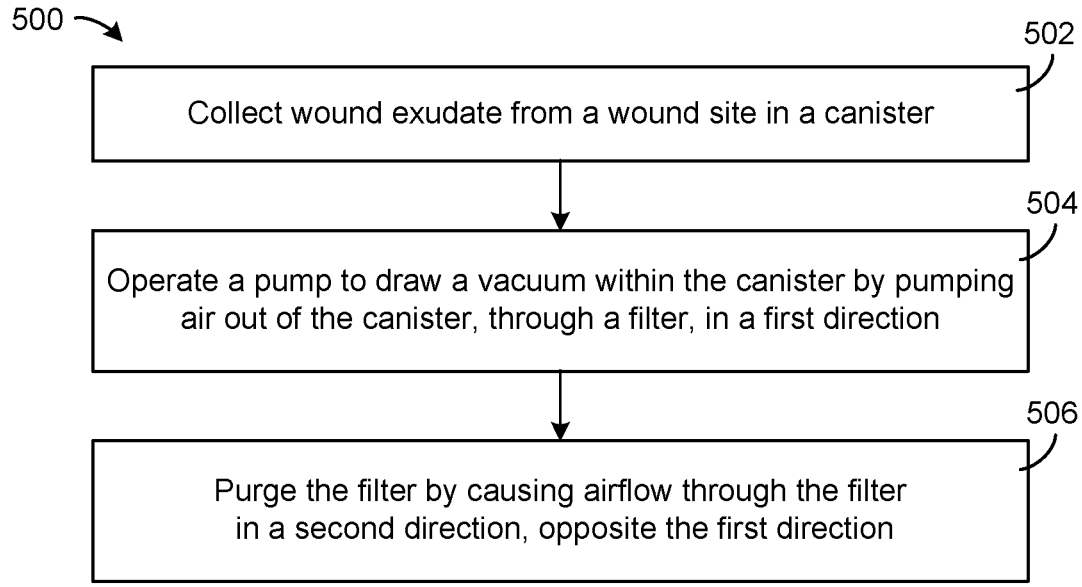
FIG. 5 is a flowchart of a process for operating the NPWT device of FIG. 1, according to an exemplary embodiment.

Referring now to FIG. 5, a flowchart of a process 500 for operating a negative pressure wound therapy (NPWT) device is shown, according to an exemplary embodiment. Process 500 can be performed by one or more components of NPWT system 100, as described with reference to FIGS. 1-4. For example, process 500 can be performed by therapy device 102 using control unit 114 to operate pump 120 and/or valve 118.

Process 500 is shown to include collecting wound exudate from a wound site in a canister (step 502) and operating a pump to draw a vacuum within the canister (step 504). In some embodiments, the vacuum is drawn within the canister by pumping air out of the canister (e.g., by operating pump 120). The air pumped out of the canister may pass through a filter (e.g., filter 122) in a first direction. For example, pump 120 can be operated as shown in FIG. 2 to pump air from canister 104, through filter 122, and into conduit 134 leading to pump 120. In some embodiments, air is pumped out of canister 104 until the pressure within canister 104 reaches a target pressure value.

Process 500 is shown to include purging the filter by causing airflow through the filter in a second direction, opposite the first direction (step 506). Step 506 can be performed by operating pump 120 and/or valve 118 to cause reverse airflow through filter 122. In some embodiment, step 506 includes closing valve 118 and operating pump 120 to draw a vacuum within conduit 134 and canister 104. After a vacuum has been drawn within canister 104, valve 118 can be opened to allow airflow into conduit 134 from the environment around therapy device 102. The airflow may fill the vacuum within conduit 134 and may pass through filter 122 in a reverse direction to fill the vacuum within canister 104, thereby purging filter 122. In other embodiments, step 506 includes purging filter 122 without operating valve 118. For example, step 506 can include operating pump 120 in a reverse direction to cause reverse airflow through filter 122, thereby purging filter 122.

Figure 6:
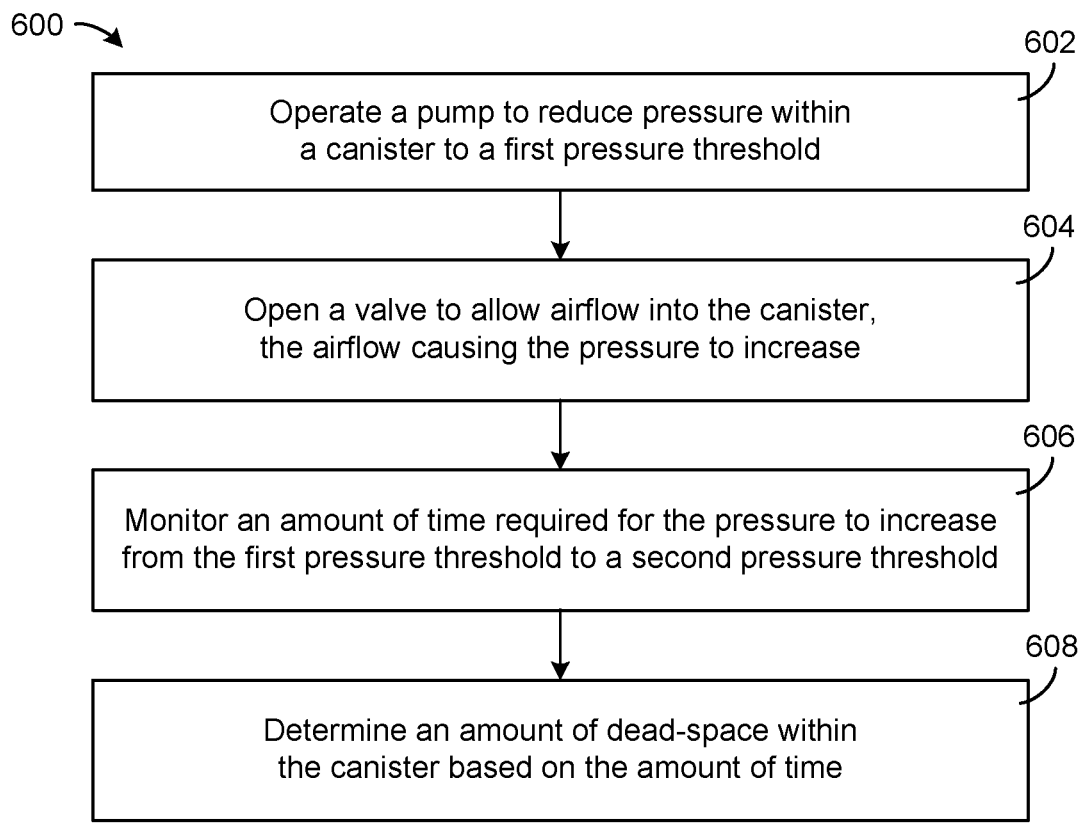
FIG. 6 is a flowchart of a process for detecting an amount of dead-space in a canister of the NPWT device of FIG. 1, according to an exemplary embodiment.

Referring now to FIG. 6, a flowchart of a process 600 for detecting an amount of dead-space in a canister of a negative pressure wound therapy (NPWT) device is shown, according to an exemplary embodiment. Process 600 can be performed by one or more components of NPWT system 100, as described with reference to FIGS. 1-4. For example, process 600 can be performed by therapy device 102 using control unit 114 to operate pump 120 and/or valve 118.

Process 600 is shown to include operating a pump (e.g., pump 120) to reduce pressure within a canister (e.g., canister 104) to a first pressure threshold (step 602). In some embodiments, step 602 includes operating pump 120 to pump air out of canister 104 until the pressure within canister 104 reaches the first pressure threshold. The pressure within canister 104 can be measured by a pressure sensor 124 installed in canister 104. Alternatively, step 602 may include operating pump 120 to pump air out of canister 104 until the pressure at wound site 106 reaches the first pressure threshold. The pressure at wound site 106 can be measured by a pressure sensor 126 installed at wound site 106.

Process 600 is shown to include opening a valve (e.g., valve 118) to allow airflow into the canister (step 604). Valve 118 can be configured to control airflow into therapy device 102 and/or canister 104 from the environment around therapy device 102. In some embodiments, step 604 includes setting valve 118 to a position at which airflow through valve 118 occurs at a known rate (e.g., a predetermined rate), or a rate that can be calculated based on the pressure difference between atmospheric pressure and the reduced pressure within canister 104. By allowing airflow into canister 104, the pressure within canister 104 may increase.

Process 600 is shown to include monitoring an amount of time required for the pressure to increase from the first pressure threshold to a second pressure threshold (step 606). The pressure within canister 104 can be measured by a pressure sensor 124 installed in canister 104. Step 606 may include recording the time at which the measured pressure reaches the second pressure threshold and subtracting the time at which valve 118 was opened to calculate the amount of time required for the pressure within canister 104 to change from the first pressure threshold to the second pressure threshold.

Process 600 is shown to include determining an amount of dead-space within the canister based on the amount of time (step 608). In some embodiments, the amount of dead-space within canister 104 is proportional (or otherwise related) to the amount of time required for the pressure within canister 104 to increase from the first pressure threshold to the second pressure threshold. For example, a canister with a large amount of dead-space may require a longer time for the pressure to increase to the second pressure threshold, whereas a canister with a smaller amount of dead-space may require a shorter time for the pressure to increase to the second pressure threshold. In some embodiments, the relationship between dead-space and time for the pressure change to occur is defined by a function, lookup table, or other relational information stored within control unit 114. Control unit 114 can use the stored relationship to translate the measured amount of time into a dead-space value.

Figure 7:
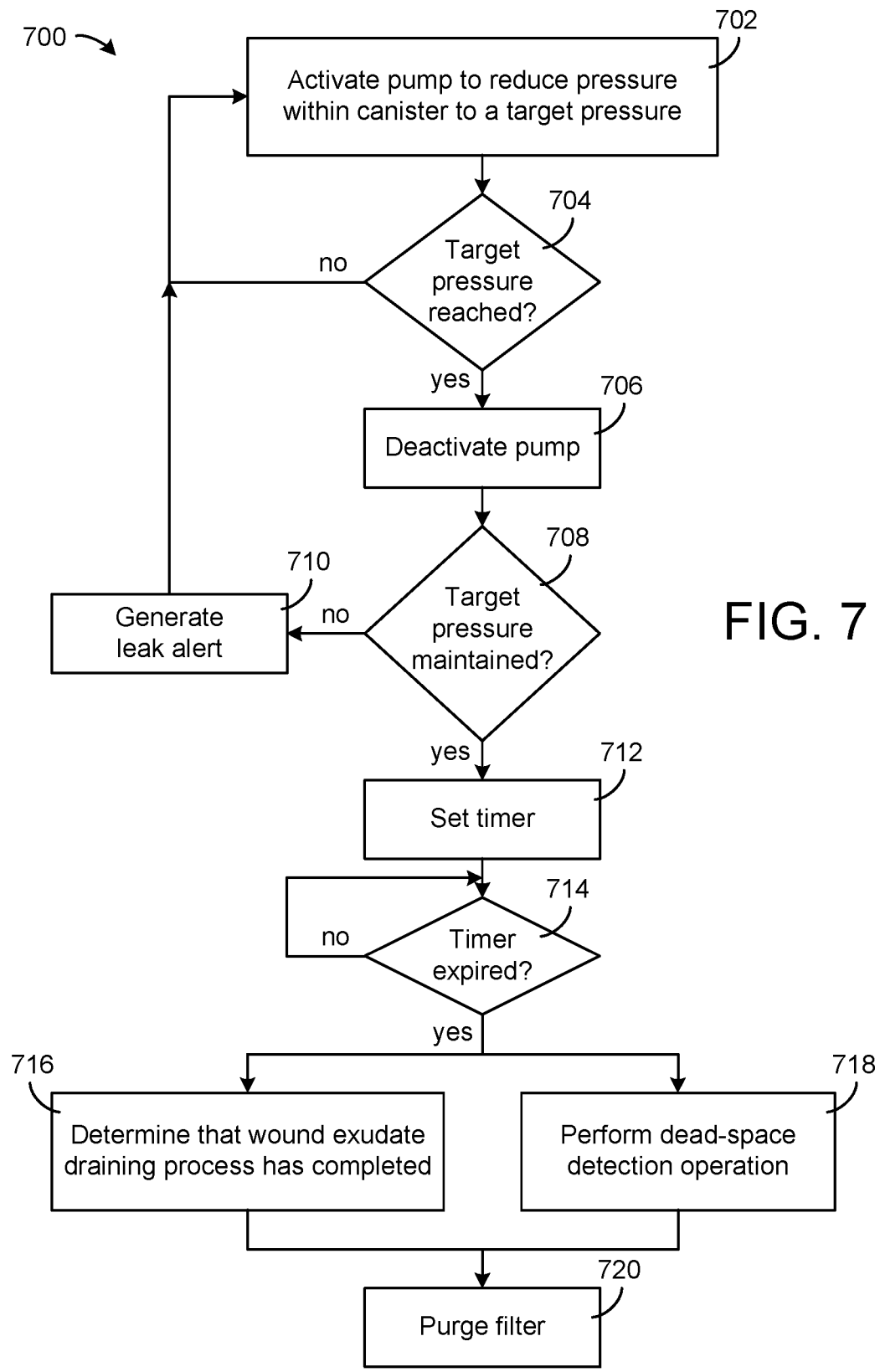
FIG. 7 is a flowchart of a process for purging a filter in the NPWT device of FIG. 1, according to an exemplary embodiment.

Referring now to FIG. 7, a flowchart of a process 700 for purging a filter in a negative pressure wound therapy (NPWT) device is shown, according to an exemplary embodiment. Process 700 can be performed by one or more components of NPWT system 100, as described with reference to FIGS. 1-4. For example, process 700 can be performed by therapy device 102 using control unit 114 to operate pump 120 and/or valve 118.

Process 700 is shown to include activating a pump (e.g., pump 120) to reduce the pressure within a canister (e.g., canister 104) to a target pressure (step 702). Pump 120 may remain active until a target pressure has been reached (step 704). Once the target pressure has been reached, pump 120 can be deactivated (step 706). After pump 120 is deactivated, pressure measurements from pressure sensor 124 can be monitored over time to determine whether the target pressure is maintained (step 708). The target pressure may be deemed maintained if the pressure within canister 104 does not change by a given amount (e.g., a percentage of the target pressure) within a predetermined amount of time after pump 120 is deactivated.

If the target pressure is not maintained, process 700 may include generating a leak alert (step 710) and returning to step 702. The leak alert can be presented to a user via a user interface 110 of therapy device 102 and/or communicated to an external system or device via communications interface 112. However, if the target pressure is maintained, control unit 114 may set a timer (step 712) and wait until the timer has expired (step 714). If the timer expires and the target pressure is still maintained, control unit 114 may determine that a wound exudate draining process has completed (step 716). Draining wound exudate from wound site 106 into canister 104 may cause the pressure within canister 104 to increase. Accordingly, maintaining the target pressure within canister 104 may indicate that wound exudate is no longer draining.

Process 700 is shown to include performing a dead-space detection operation (step 718). In some embodiments, the dead-space detection operation is performed in response to a determination that the target pressure is maintained for the predetermined amount of time and/or in response to a determination that the wound exudate draining process has completed. Step 718 can be accomplished by performing process 600, as described with reference to FIG. 6.

Process 700 is shown to include purging the filter (step 720). In some embodiments, step 720 includes causing airflow through filter 122 in a reverse direction. Step 720 can be performed by operating pump 120 and/or valve 118 to cause reverse airflow through filter 122. In some embodiment, step 720 includes closing valve 118 and operating pump 120 to draw a vacuum within conduit 134 and canister 104. After a vacuum has been drawn within canister 104, valve 118 can be opened to allow airflow into conduit 134 from the environment around therapy device 102. The airflow may fill the vacuum within conduit 134 and may pass through filter 122 in a reverse direction to fill the vacuum within canister 104, thereby purging filter 122. In other embodiments, step 720 includes purging filter 122 without operating valve 118. For example, step 720 can include operating pump 120 in a reverse direction to cause reverse airflow through filter 122, thereby purging filter 122.

Figure 8:
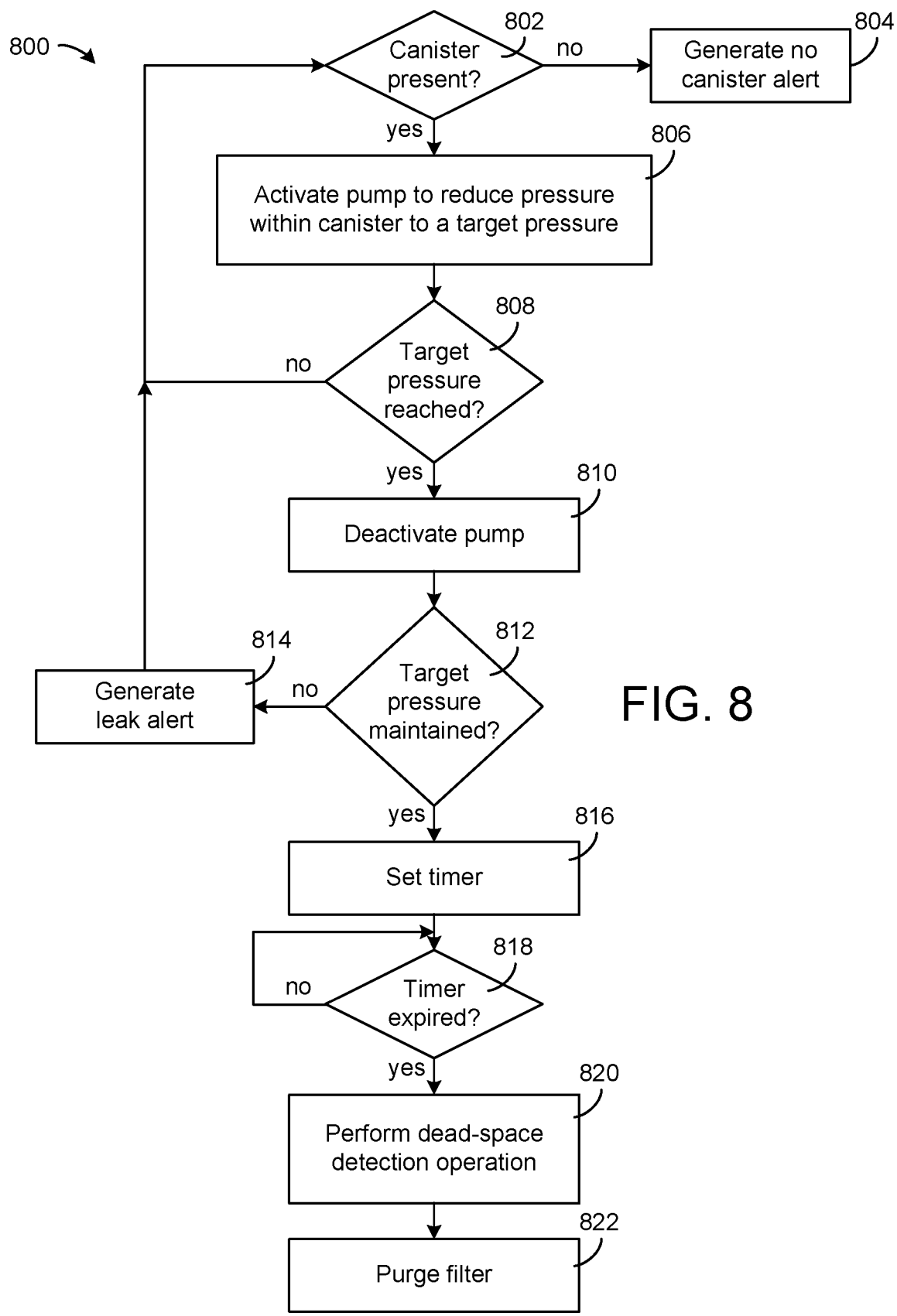
FIG. 8 is a flowchart of another process for purging a filter in the NPWT device of FIG. 1, according to an exemplary embodiment.

Referring now to FIG. 8, a flowchart of a process 800 for purging a filter in a negative pressure wound therapy (NPWT) device is shown, according to an exemplary embodiment. Process 800 can be performed by one or more components of NPWT system 100, as described with reference to FIGS. 1-4. For example, process 800 can be performed by therapy device 102 using control unit 114 to operate pump 120 and/or valve 118. Process 800 may be similar to process 700, with the exception that process 800 requires canister 104 to be present before subsequent steps of process 800 are performed.

Process 800 is shown to include determining whether a canister is present (step 802). In some embodiments, step 802 includes using input from a canister sensor to determine whether canister 104 is currently located in therapy device 102. If canister 104 is not present, control unit 114 may generate a "no canister" alert (step 804). The no canister alert can be presented to a user via a user interface 110 of therapy device 102 and/or communicated to an external system or device via communications interface 112. However, if canister 104 is present, process 800 may proceed to step 806.

Process 800 is shown to include activating a pump (e.g., pump 120) to reduce the pressure within the canister to a target pressure (step 806). Pump 120 may remain active until a target pressure has been reached (step 808). Once the target pressure has been reached, pump 120 can be deactivated (step 810). After pump 120 is deactivated, pressure measurements from pressure sensor 124 can be monitored over time to determine whether the target pressure is maintained (step 812). The target pressure may be deemed maintained if the pressure within canister 104 does not change by a given amount (e.g., a percentage of the target pressure) within a predetermined amount of time after pump 120 is deactivated.

If the target pressure is not maintained, process 800 may include generating a leak alert (step 814) and returning to step 802. The leak alert can be presented to a user via a user interface 110 of therapy device 102 and/or communicated to an external system or device via communications interface 112. However, if the target pressure is maintained, control unit 114 may set a timer (step 816) and wait until the timer has expired (step 818). If the timer expires and the target pressure is still maintained, control unit 114 may perform a dead-space detection operation (step 820). In some embodiments, the dead-space detection operation is performed in response to a determination that the target pressure is maintained for the predetermined amount of time and/or in response to a determination that the wound exudate draining process has completed. Step 820 can be accomplished by performing process 600, as described with reference to FIG. 6.

Process 800 is shown to include purging the filter (step 822). In some embodiments, step 822 includes causing airflow through filter 122 in a reverse direction. Step 822 can be performed by operating pump 120 and/or valve 118 to cause reverse airflow through filter 122. In some embodiment, step 822 includes closing valve 118 and operating pump 120 to draw a vacuum within conduit 134 and canister 104. After a vacuum has been drawn within canister 104, valve 118 can be opened to allow airflow into conduit 134 from the environment around therapy device 102. The airflow may fill the vacuum within conduit 134 and may pass through filter 122 in a reverse direction to fill the vacuum within canister 104, thereby purging filter 122. In other embodiments, step 822 includes purging filter 122 without operating valve 118. For example, step 822 can include operating pump 120 in a reverse direction to cause reverse airflow through filter 122, thereby purging filter 122.

Figure 9:
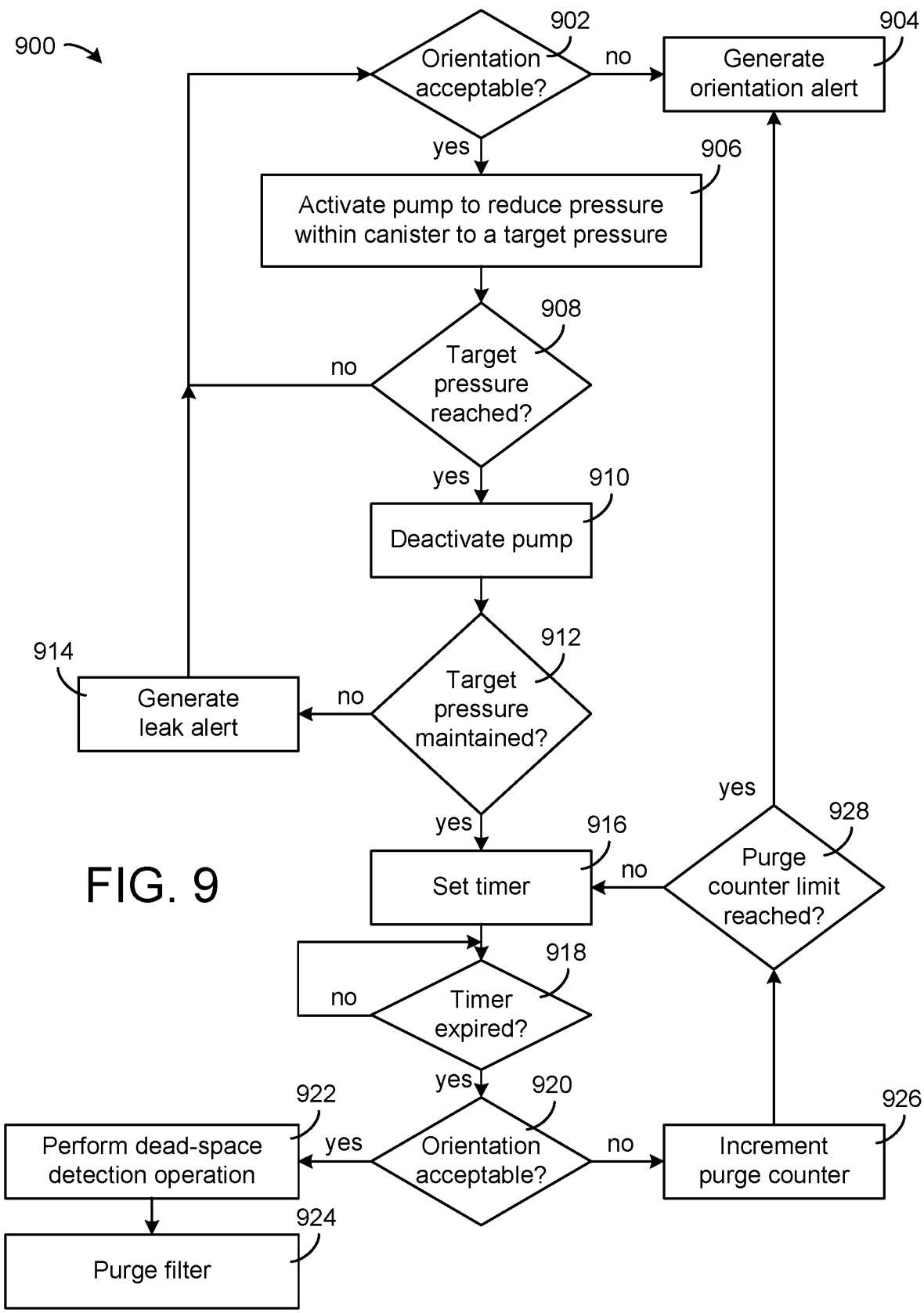
FIG. 9 is a flowchart of another process for purging a filter in the NPWT device of FIG. 1, according to an exemplary embodiment.

Referring now to FIG. 9, a flowchart of a process 900 for purging a filter in a negative pressure wound therapy (NPWT) device is shown, according to an exemplary embodiment. Process 900 can be performed by one or more components of NPWT system 100, as described with reference to FIGS. 1-4. For example, process 900 can be performed by therapy device 102 using control unit 114 to operate pump 120 and/or valve 118. Process 900 may be similar to process 700, with the exception that process 900 requires the orientation of canister 104 and/or therapy device 102 to be acceptable before subsequent steps of process 900 are performed.

Process 900 is shown to include determining whether the orientation of therapy device 102 and/or canister 104 is acceptable (step 902). An acceptable orientation can be defined as an orientation that is substantially upright (e.g., within a predetermined angle from upright), whereas an unacceptable orientation can be defined as an orientation that is not upright or substantially tilted relative to upright. In some embodiments, step 902 includes using input from orientation sensor 132 to determine the orientation of therapy device 102 and/or canister 104 relative to the direction of gravity. If the orientation is not acceptable, control unit 114 may generate an orientation alert (step 904). The orientation alert can be presented to a user via a user interface 110 of therapy device 102 and/or communicated to an external system or device via communications interface 112. However, if the orientation is acceptable, process 900 may proceed to step 906.

Process 900 is shown to include activating a pump (e.g., pump 120) to reduce the pressure within the canister to a target pressure (step 906). Pump 120 may remain active until a target pressure has been reached (step 908). Once the target pressure has been reached, pump 120 can be deactivated (step 910). After pump 120 is deactivated, pressure measurements from pressure sensor 124 can be monitored over time to determine whether the target pressure is maintained (step 912). The target pressure may be deemed maintained if the pressure within canister 104 does not change by a given amount (e.g., a percentage of the target pressure) within a predetermined amount of time after pump 120 is deactivated.

If the target pressure is not maintained, process 900 may include generating a leak alert (step 914) and returning to step 902. The leak alert can be presented to a user via a user interface 110 of therapy device 102 and/or communicated to an external system or device via communications interface 112. However, if the target pressure is maintained, control unit 114 may set a timer (step 916) and wait until the timer has expired (step 918). If the timer expires and the target pressure is still maintained, control unit 114 may once again determine whether the orientation of therapy device 102 and/or canister 104 is acceptable (step 920).

If the orientation is not acceptable, control unit 114 my increment a purge counter (step 926) and determine whether the purge counter has reached a purge counter limit (step 928). If the purge counter limit has been reached, control unit 114 may generate an orientation alert (step 904). However, if the purge counter limit has not been reached, process 900 may return to step 916. Steps 916-920 and steps 926-928 may be repeated until either the orientation is found to be acceptable in step 920 or the purge counter limit has been reached in step 928. If the orientation is acceptable in step 920, the purge counter may be reset to zero and process 900 may proceed to step 922.

Process 900 is shown to include performing a dead-space detection operation (step 922). In some embodiments, the dead-space detection operation is performed in response to a determination that the target pressure is maintained for the predetermined amount of time and/or in response to a determination that the wound exudate draining process has completed. Step 922 can be accomplished by performing process 600, as described with reference to FIG. 6.

Process 900 is shown to include purging the filter (step 924). In some embodiments, step 924 includes causing airflow through filter 122 in a reverse direction. Step 924 can be performed by operating pump 120 and/or valve 118 to cause reverse airflow through filter 122. In some embodiment, step 924 includes closing valve 118 and operating pump 120 to draw a vacuum within conduit 134 and canister 104. After a vacuum has been drawn within canister 104, valve 118 can be opened to allow airflow into conduit 134 from the environment around therapy device 102. The airflow may fill the vacuum within conduit 134 and may pass through filter 122 in a reverse direction to fill the vacuum within canister 104, thereby purging filter 122. In other embodiments, step 924 includes purging filter 122 without operating valve 118. For example, step 924 can include operating pump 120 in a reverse direction to cause reverse airflow through filter 122, thereby purging filter 122.

Figure 10:
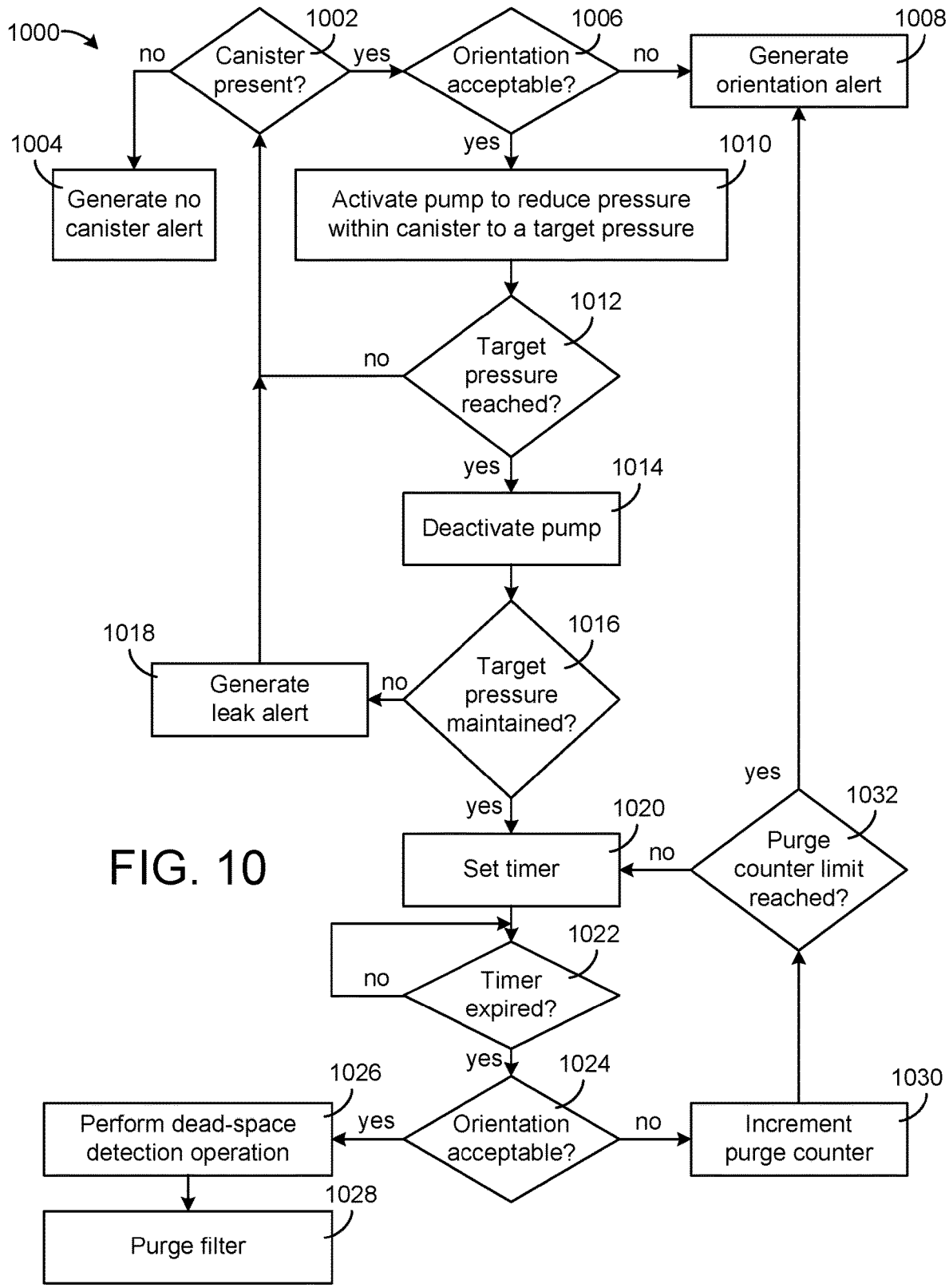
FIG. 10 is a flowchart of another process for purging a filter in the NPWT device of FIG. 1, according to an exemplary embodiment.

Referring now to FIG. 10, a flowchart of a process 1000 for purging a filter in a negative pressure wound therapy (NPWT) device is shown, according to an exemplary embodiment. Process 1000 can be performed by one or more components of NPWT system 100, as described with reference to FIGS. 1-4. For example, process 1000 can be performed by therapy device 102 using control unit 114 to operate pump 120 and/or valve 118. Process 1000 may be similar to process 700, with the exception that process 1000 requires both canister 104 to be present and the orientation of canister 104 and/or therapy device 102 to be acceptable before subsequent steps of process 1000 are performed.

Process 1000 is shown to include determining whether a canister is present (step 1002). In some embodiments, step 1002 includes using input from a canister sensor to determine whether canister 104 is currently located in therapy device 102. If canister 104 is not present, control unit 114 may generate a "no canister" alert (step 1004). The no canister alert can be presented to a user via a user interface 110 of therapy device 102 and/or communicated to an external system or device via communications interface 112. However, if canister 104 is present, process 1000 may proceed to step 1006.

Process 900 is shown to include determining whether the orientation of therapy device 102 and/or canister 104 is acceptable (step 1006). An acceptable orientation can be defined as an orientation that is substantially upright (e.g., within a predetermined angle from upright), whereas an unacceptable orientation can be defined as an orientation that is not upright or substantially tilted relative to upright. In some embodiments, step 1006 includes using input from orientation sensor 132 to determine the orientation of therapy device 102 and/or canister 104 relative to the direction of gravity. If the orientation is not acceptable, control unit 114 may generate an orientation alert (step 1008). The orientation alert can be presented to a user via a user interface 110 of therapy device 102 and/or communicated to an external system or device via communications interface 112. However, if the orientation is acceptable, process 1000 may proceed to step 1010.

Process 1000 is shown to include activating a pump (e.g., pump 120) to reduce the pressure within the canister to a target pressure (step 1010). Pump 120 may remain active until a target pressure has been reached (step 1012). Once the target pressure has been reached, pump 120 can be deactivated (step 1014). After pump 120 is deactivated, pressure measurements from pressure sensor 124 can be monitored over time to determine whether the target pressure is maintained (step 1016). The target pressure may be deemed maintained if the pressure within canister 104 does not change by a given amount (e.g., a percentage of the target pressure) within a predetermined amount of time after pump 120 is deactivated.

If the target pressure is not maintained, process 1000 may include generating a leak alert (step 1018) and returning to step 1002. The leak alert can be presented to a user via a user interface 110 of therapy device 102 and/or communicated to an external system or device via communications interface 112. However, if the target pressure is maintained, control unit 114 may set a timer (step 1020) and wait until the timer has expired (step 1022). If the timer expires and the target pressure is still maintained, control unit 114 may once again determine whether the orientation of therapy device 102 and/or canister 104 is acceptable (step 1024).

If the orientation is not acceptable, control unit 114 my increment a purge counter (step 1030) and determine whether the purge counter has reached a purge counter limit (step 1032). If the purge counter limit has been reached, control unit 114 may generate an orientation alert (step 1008). However, if the purge counter limit has not been reached, process 1000 may return to step 1020. Steps 1020-1024 and steps 1030-1032 may be repeated until either the orientation is found to be acceptable in step 1024 or the purge counter limit has been reached in step 1032. If the orientation is acceptable in step 1024, the purge counter may be reset to zero and process 1000 may proceed to step 1026.

Process 1000 is shown to include performing a dead-space detection operation (step 1026). In some embodiments, the dead-space detection operation is performed in response to a determination that the target pressure is maintained for the predetermined amount of time and/or in response to a determination that the wound exudate draining process has completed. Step 1026 can be accomplished by performing process 600, as described with reference to FIG. 6.

Process 1000 is shown to include purging the filter (step 1028). In some embodiments, step 1028 includes causing airflow through filter 122 in a reverse direction. Step 1028 can be performed by operating pump 120 and/or valve 118 to cause reverse airflow through filter 122. In some embodiment, step 1028 includes closing valve 118 and operating pump 120 to draw a vacuum within conduit 134 and canister 104. After a vacuum has been drawn within canister 104, valve 118 can be opened to allow airflow into conduit 134 from the environment around therapy device 102. The airflow may fill the vacuum within conduit 134 and may pass through filter 122 in a reverse direction to fill the vacuum within canister 104, thereby purging filter 122. In other embodiments, step 1028 includes purging filter 122 without operating valve 118. For example, step 1028 can include operating pump 120 in a reverse direction to cause reverse airflow through filter 122, thereby purging filter 122.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A negative pressure wound therapy device comprising:
   a canister configured to collect wound exudate from a wound site;
   a pump fluidly coupled to the canister and configured to draw a vacuum within the canister by pumping air out of the canister;
   a filter positioned between the canister and the pump such that the air pumped out of the canister passes through the filter in a first direction; and
   a control unit configured to operate the pump and to purge the filter by causing airflow through the filter in a second direction, opposite the first direction.

2. The negative pressure wound therapy device of claim 1, further comprising a purge valve fluidly connected with the pump and the filter;
   wherein the control unit is configured to operate the purge valve to cause the airflow through the filter in the second direction.

3. The negative pressure wound therapy device of claim 2, wherein the control unit is configured to purge the filter by:
   operating the pump to draw a vacuum within the canister; and
   opening the purge valve to allow airflow into the canister, the airflow filling the vacuum within the canister and passing through the filter in the second direction.

4. The negative pressure wound therapy device of claim 2, wherein the control unit is configured to determine an amount of dead-space within the canister by:
   operating the pump to reduce a pressure within the canister to a first pressure threshold;
   opening the purge valve to allow airflow into the canister, the airflow causing the pressure within the canister to increase;
   monitoring an amount of time required for the pressure within the canister to increase from the first pressure threshold to a second pressure threshold; and
   determining the amount of dead-space within the canister based on the amount of time;
   wherein the dead-space within the canister comprises an internal volume of the canister not occupied by the wound exudate.

5. The negative pressure wound therapy device of claim 1, wherein the control unit is configured to:

operate the pump in a forward operating mode to cause the airflow through the filter in the first direction; and operate the pump in a reverse operating mode to cause the airflow through the filter in the second direction.

6. The negative pressure wound therapy device of Claim 1, further comprising a pressure sensor configured to measure a pressure within the canister or at the wound site, and wherein the control unit is configured to:

activate the pump to reduce the measured pressure to a target pressure;

deactivate the pump upon detecting that the measured pressure has reached the target pressure;

determine whether the target pressure is maintained for a predetermined amount of time after deactivating the pump; and in response to a determination that the target pressure is maintained for the predetermined amount of time, purge the filter by causing the airflow through the filter in a second direction.

7. The negative pressure wound therapy device of claim 6, wherein the control unit is configured to:

determine that a wound exudate draining process has completed in response to the determination that the target pressure is maintained for the predetermined amount of time; and purge the filter in response to a determination that the draining process has completed.

8. The negative pressure wound therapy device of claim 6, wherein the control unit is configured to:

perform a dead-space detection operation to determine an amount of dead-space within the canister in response to the determination that the target pressure is maintained for the predetermined amount of time; and purge the filter after performing the dead-space detection operation.

9. The negative pressure wound therapy device of claim 6, further comprising a canister sensor configured to detect whether the canister is present;

wherein the control unit is configured to determine whether the canister is present based on input from the canister sensor and activate the pump in response to a determination that the canister is present.

10. The negative pressure wound therapy device of claim 6, further comprising an orientation sensor configured to detect an orientation of at least one of the canister or the negative pressure wound therapy device;

wherein the control unit is configured to determine the orientation based on input from the orientation sensor and activate the pump in response to a determination that the orientation is acceptable.

11. The negative pressure wound therapy device of claim 10, wherein the orientation sensor is an accelerometer configured to measure the orientation relative to a direction of gravity.

12. The negative pressure wound therapy device of claim 10, wherein the control unit is configured to:

start a timer in response to a determination that the orientation is not acceptable; and upon expiration of the timer, use new input from the orientation sensor to determine whether the orientation is acceptable.

13. The negative pressure wound therapy device of claim 10, wherein the control unit is configured to:

increment a counter in response to a determination that the orientation is not acceptable;

compare the counter to a threshold value; and generate an orientation alert in response to a determination that the counter has reached the threshold value.

* * * * *